(12) United States Patent
Andersson et al.

(10) Patent No.: US 6,534,653 B2
(45) Date of Patent: Mar. 18, 2003

(54) 3,5-DIOXA-8-AZA-TRICYCLO[5.2.1.0⁰,⁰] DECANE-9-METHANOLS, THEIR METAL COMPLEXES AND ENANTIO-SELECTIVE HYDROGENATION PROCESSES

(75) Inventors: Pher G. Andersson, Uppsala (SE); Sofia J. M. Nordin, Uppsala (SE); Peter Roth, Uppsala (SE)

(73) Assignee: Solvias AG, Basel (CH)

( * ) Notice: Subject to any disclaimer, the term of this patent is extended or adjusted under 35 U.S.C. 154(b) by 31 days.

(21) Appl. No.: 09/828,882

(22) Filed: Apr. 10, 2001

(65) Prior Publication Data
US 2002/0061815 A1 May 23, 2002

(30) Foreign Application Priority Data
Apr. 13, 2000 (CH) ................................. 734/00

(51) Int. Cl.⁷ ......................... C07F 7/02; C07D 491/02
(52) U.S. Cl. ........................................... 546/14; 546/90
(58) Field of Search ...................... 546/14, 90

(56) References Cited

U.S. PATENT DOCUMENTS 6,051,711 A * 4/2000 Tropper et al. ............... 546/90

FOREIGN PATENT DOCUMENTS

| CA | 2239970 | 6/1997 |
| WO | 98/42643 | 10/1998 |

OTHER PUBLICATIONS

Pinho, P., et al. "A novel synthesis of chiral cyclopentyl– and cyclohexyl–amines", Chem. Commun., (1999), pp. 597–598.

Alonso, D.A., et al. "(1S,3R,4R)–2–Azanorbornylmethanol, an Efficient Ligand for Ruthenium–Catalyzed Asymmetric Transfer Hydrogenation of Ketones", J. Org. Chem., vol. 63 (1998), pp. 2749–2751.

* cited by examiner

Primary Examiner—Deborah C. Lambkin
(74) Attorney, Agent, or Firm—Wenderoth, Lind & Ponack, L.L.P.

(57) ABSTRACT

Compounds of the formula I, in the form of their racemates, mixtures of stereoisomers or mainly pure stereoisomers

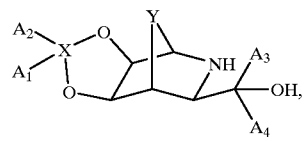

(I)

in which

Y is $C_1$–$C_4$alkylene or —$SiR_1R_2$—;

X is a carbon atom and $A_1$ and $A_2$ independently of one another are hydrogen, $C_1$–$C_{12}$alkyl, $C_2$–$C_{12}$alkenyl, $C_3$–$C_8$cycloalkyl, $C_3$–$C_8$cycloalkenyl, $C_3$–$C_8$cycloalkyl-$C_1$–$C_4$alkyl, $C_3$–$C_8$cycloalkenyl-$C_1$–$C_4$alkyl, $C_6$–$C_{10}$aryl or $C_7$–$C_{14}$aralkyl; or X is a silicon atom and $A_1$ and $A_2$ independently of one another are $C_1$–$C_{12}$alkyl, $C_3$–$C_8$cycloalkyl, $C_3$–$C_8$cycloalkyl-$C_1$–$C_4$alkyl, $C_6$–$C_{10}$aryl or $C_7$–$C_{14}$aralkyl;

$A_3$ and $A_4$ independently of one another are hydrogen, $C_1$–$C_{12}$alkyl, $C_3$–$C_8$cycloalkyl, $C_3$–$C_8$-cycloalkyl-$C_1$–$C_4$alkyl, $C_6$–$C_{10}$aryl or $C_7$–$C_{14}$aralkyl; and $R_1$ and $R_2$ independently of one another are $C_1$–$C_6$alkyl, cyclohexyl, phenyl or benzyl, are ligands for metal complexes of the eighth sub-group of the Periodic Table of the Elements, which are suitable as catalysts for asymmetric hydrogenations and transfer hydrogenations of prochiral compounds having carbon/carbon or carbon/heteroatom multiple bonds.

21 Claims, No Drawings

3,5-DIOXA-8-AZA-TRICYCLO[5.2.1.0⁰,⁰] DECANE-9-METHANOLS, THEIR METAL COMPLEXES AND ENANTIO-SELECTIVE HYDROGENATION PROCESSES

The present invention relates to 8-azadioxolanebicyclomethanols; metal complexes with metals selected from the eighth sub-group of the Periodic Table of the Elements (subsequently designated as TM8 metals) and 8-azadioxolanebicyclomethanols as ligands; a process for the asymmetric transfer hydrogenation of prochiral carbon double bonds or heteroatom carbon double bonds using hydrogen or hydrogen donors; the use of metal complexes with TM8 metals and azadioxolanebicyclomethanols as ligands for the asymmetric transfer hydrogenation of prochiral carbon and heteroatom carbon double bonds; and a kit formed from (a) a TM8 metal compound as precursor for a metal complex and (b) 8-azadioxolanebicyclomethanols as ligands, the components (a) and (b) being located in separate vessels.

CA-A-2,239,970 describes a process for the asymmetric hydrogenation of C-heteroatom double bonds in, for example, prochiral ketones or imines using inorganic or organic hydrogen donors, for example secondary alcohols, in which transition metal complexes are employed as enanantioselective catalysts which contain compounds comprising chiral nitrogen as ligands. In the description, the ligands having a 1,2-aminoethanol parent structure are mentioned. Good optical yields are achieved. The low catalyst activity causes long reaction times and the use of relatively high amounts of catalyst, which stands in the way of industrial application.

WO 98/42643 describes the same process, identical or similar ligands being used, and Ru, Rh and iridium complexes with substituted cyclopentadienyl ligands being employed as catalysts. The disadvantages mentioned beforehand also exist here.

In J. Org. Chem. 1998, 63, pages 2749 to 2751, D. A. Alonso et al. also describe the process mentioned, 2-aza-1-hydroxymethyinorbornane being used as bicyclic asymmetric ligand. Using this ligand, high optical yields are in turn achieved, the catalyst activity, however, being felt to be inadequate.

It has now surprisingly been found that high conversions can be achieved in asymmetric transfer hydrogenation using chiral 8-aza-1-hydroxymethylnorbornanes as ligands in TM8 metal complexes as catalysts in significantly shorter reaction times and high optical yields even with relatively low amounts of catalyst if a dioxolane ring is fused to the bicyclic ring system.

A first subject of the invention is compounds of the formula I, in the form of their racemates, mixtures of stereoisomers or mainly pure stereoisomers,

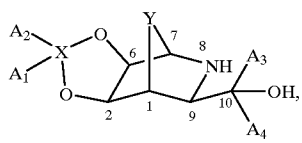

(I)

in which
Y is $C_1$–$C_4$alkylene or —$SiR_1R_2$—;
X is a carbon atom and $A_1$ and $A_2$ independently of one another are hydrogen, $C_1$–$C_{12}$alkyl, $C_2$–$C_{12}$alkenyl, $C_3$–$C_8$cycloalkyl, $C_3$–$C_8$cycloalkenyl, $C_3$–$C_8$cycloalkyl-$C_1$–$C_4$alkyl, $C_3$–$C_8$cycloalkenyl-$C_1$–$C_4$alkyl, $C_6$–$C_{10}$aryl or $C_7$–$C_{14}$aralkyl; or X is a silicon atom and $A_1$ and $A_2$ independently of one another are $C_1$–$C_{12}$alkyl, $C_3$–$C_8$cycloalkyl, $C_3$–$C_8$cycloalkyl-$C_1$–$C_4$alkyl, $C_6$–$C_{10}$aryl or $C_7$–$C_{14}$aralkyl;

$A_3$ and $A_4$ independently of one another are hydrogen, $C_1$–$C_{12}$alkyl, $C_3$–$C_8$cycloalkyl, $C_3$–$C_8$cycloalkyl-$C_1$–$C_4$alkyl, $C_6$–$C_{10}$aryl or $C_7$–$C_{14}$aralkyl; and $R_1$ and $R_2$ independently of one another are $C_1$–$C_6$alkyl, cyclohexyl, phenyl or benzyl.

Among the stereoisomers, those having the configuration 1S, 2R, 6S, 7R, 9R are preferred. Among the enantiomers, those having the configuration 1S, 2R, 6S, 7R, 9R, 10R are preferred.

$R_1$ and $R_2$ are preferably independently of one another linear $C_1$–$C_4$alkyl. In formula I, Y is preferably linear or branched alkylene, and particularly preferably methylene or ethylene.

In formula I, X is preferably a carbon atom. $A_1$ and $A_2$ are preferably identical radicals.

As alkyl, $A_1$ and $A_2$ preferably contain 1 to 6 and particularly preferably 1 to 4 C atoms. Examples of alkyl are methyl, ethyl, n- and i-propyl, n-, i- and t-butyl, and the isomers of pentyl and hexyl.

As alkenyl, $A_1$ and $A_2$ preferably contain 2 to 6 and particularly preferably 2 to 4 C atoms. Examples of alkenyl are vinyl, allyl and crotonyl.

As cycloalkyl, $A_1$ and $A_2$ preferably contain 4 to 7 and particularly preferably 5 or 6 ring C atoms. Examples of cycolalkyl are cyclopropyl, cyclobutyl, cyclopentyl, cyclohexyl, cycloheptyl and cyclooctyl. Cyclopentyl and cyclohexyl are preferred.

As cycloalkenyl, $A_1$ and $A_2$ preferably contain 4 to 7 and particularly preferably 5 or 6 ring C atoms. Examples of cycloalkenyl are cyclopropenyl, cyclobutenyl, cyclopentenyl, cyclohexenyl, cycloheptenyl and cyclooctenyl. Cyclopentenyl and cyclohexenyl are preferred.

As cycloalkylalkyl, $A_1$ and $A_2$ are preferably $C_5$–$C_6$cycloalkyl-$C_1$–$C_2$alkyl. Examples are cyclopentylmethyl, cyclohexylmethyl, cyclopentylethyl and cyclohexylethyl.

As cycloalkenylalkyl, $A_1$ and $A_2$ are preferably $C_5$–$C_6$cycloalkenyl-$C_1$–$C_2$alkyl. Examples are cyclopentenylmethyl, cyclohexenylmethyl, cyclopentenylethyl and cyclohexenylethyl.

As aryl, $A_1$ and $A_2$ can be, for example, phenyl or naphthyl.

As aralkyl, $A_1$ and $A_2$ can be, for example, phenyl-$C_1$–$C_4$alkyl or naphthyl-$C_1$–$C_4$alkyl. Benzyl and phenylethyl are preferred.

In a preferred embodiment, $A_1$ and $A_2$ are hydrogen, $C_1$–$C_4$alkyl, cyclopentyl, cyclohexyl, phenyl or benzyl. Particularly preferably, $A_1$ and $A_2$ are each $C_1$–$C_4$alkyl and very particularly preferably each methyl.

If X is a silicon atom, $A_1$ and $A_2$ are preferably each methyl, ethyl or phenyl.

$A_3$ and $A_4$ can be identical or different. Preferably, $A_3$ and $A_4$ are identical and are hydrogen. Another preferred group are compounds of the formula I in which $A_3$ and $A_4$ are different, particularly those in which $A_3$ is hydrogen and $A_4$ is $C_1$–$C_{12}$alkyl, $C_3$–$C_8$cycloalkyl, $C_3$–$C_8$cycloalkyl-$C_1$–$C_4$alkyl, $C_6$–$C_{10}$aryl or $C_7$–$C_{14}$aralkyl, preferably $C_1$–$C_4$alkyl. It has surprisingly been found that the catalyst activity can be further increased if, in the ligand of the formula I, $A_3$ is hydrogen and $A_4$ is a substituent, and the chiral C atom to which $A_4$ is bonded has the R configuration, the other chiral C atoms having the configuration 1S, 2R, 6S, 7R, 9R.

As alkyl, $A_3$ and $A_4$ preferably contain 1 to 6 and particularly preferably 1 to 4 C atoms. Examples of alkyl are methyl, ethyl, n- and i-propyl, n-, i- and t-butyl, and the isomers of pentyl and hexyl. Methyl and ethyl are particularly preferred.

As cycloalkyl, $A_3$ and $A_4$ preferably contain 4 to 7 and particularly preferably 5 or 6 ring C atoms. Examples of cycloalkyl are cyclopropyl, cyclobutyl, cyclopentyl, cyclohexyl, cycloheptyl and cyclooctyl. Cyclopentyl and cyclohexyl are preferred.

As cycloalkylalkyl, $A_3$ and $A_4$ are preferably $C_5$-$C_6$cycloalkyl-$C_1$-$C_2$alkyl. Examples are cyclopentylmethyl, cyclohexylmethyl, cyclopentylethyl and cyclohexylethyl.

As aryl, $A_3$ and $A_4$ can be, for example, phenyl or naphthyl.

As aralkyl, $A_3$ and $A_4$ can be, for example, phenyl-$C_1$-$C_4$alkyl or naphthyl-$C_1$-$C_4$alkyl. Benzyl and phenylethyl are preferred.

In a preferred embodiment, $A_3$ and $A_4$ are hydrogen, methyl or ethyl.

Particularly preferred compounds of the formula I have the formula Ia

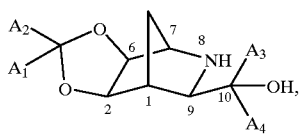

(Ia)

in which
$A_1$ and $A_2$ independently of one another are hydrogen, $C_1$-$C_4$alkyl, $C_5$-$C_6$cycloalkyl, $C_5$-$C_6$cycloalkylmethyl, phenyl or benzyl; and
$A_3$ and $A_4$ independently of one another are hydrogen or $C_1$-$C_4$alkyl.

Among the stereoisomers of the compounds of the formula Ia those having the configuration 1S, 2R, 6S, 7R, 9R are preferred. Among the enantiomers of the compounds of the formula Ia those having the configuration 1S, 2R, 6S, 7R, 9R, 10R are preferred.

In formula Ia, $A_1$ and $A_2$ are preferably hydrogen, $C_1$-$C_4$alkyl, cyclohexyl or phenyl. $A_1$ and $A_2$ are preferably each $C_1$-$C_4$alkyl, cyclohexyl or phenyl. In another preferred embodiment, $A_1$ is hydrogen and $A_2$ is $C_1$-$C_4$alkyl, cyclohexyl or phenyl.

The compounds of the formula I can be prepared according to process steps known per se from 2-azabicycloalkene-1-carboxylic acids, which for their part are accessible in a known manner by means of Diels-Alder additions of unsubstituted or N-substituted α-carboxylic acid ester imines to cyclodienes.

A further subject of the invention is a process for the preparation of compounds of the formula I, in which (a) a compound of the formula II

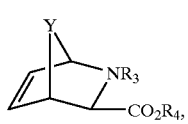

(II)

in which $R_3$ is hydrogen or a protective group, and $R_4$ is $C_1$-$C_4$alkyl, phenyl or benzyl, is reacted in an inert solvent with $OsO_4$ and subsequent hydrolysis to the cis-diol of the formula III

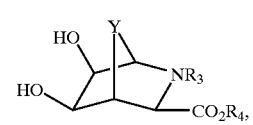

(III)

(b) the compound of the formula III is acetalized or ketalized to give a compound of the formula IV

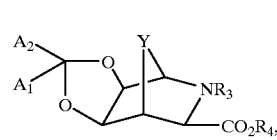

(IV)

and (c) if desired, after removal of the protective group, the compound of the formula IV is reduced to a compound of the formula I in which $A_3$ and $A_4$ are each hydrogen, (d1) or the ester group of the compound of the formula III is first reduced to the alcohol and then oxidized to the aldehyde of the formula V

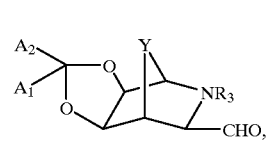

(V)

(d2) the compound of the formula V is reacted with a Grignard reagent comprising the group $A_4$ and, if desired, removal of the protective group $R_3$ to give a compound of the formula I in which $A_3$ is hydrogen and $A_4$ is a substituent with the meaning indicated beforehand.

To increase the yield of one diastereomer, it may be appropriate to oxidize the alcohols with a low content of the desired diastereomer obtained in process stage (d2) to ketones (for example using a Swern oxidation), and then to reduce them again in order to isolate the desired diastereomer from the racemate. The undesired diastereomer can be subjected to this operation directly a number of times or as a mixture with new synthesis product.

For the preparation of the compounds of the formula I in which $A_3$ and $A_4$ are a substituent, the hydroxyl group in the reaction product of process stage (d2) can first be substituted with halogen (Cl, Br or I) and then reacted with a Grignard reagent comprising the group $A_3$.

Suitable protective groups are frequently known and familiar to the person skilled in the art. Preferred protective groups are benzyl, 1-phenyl-1-ethyl, diphenylmethyl and trityl, which are easily removable catalytically using noble metal catalysts (platinum, palladium and compounds thereof) in the presence of hydrogen.

The reactions of process stages a) to d) can be carried out without or in the presence of an inert solvent, it being possible to employ one solvent or mixtures of solvents. Suitable solvents are, for example, aliphatic, cycloaliphatic and aromatic hydrocarbons (pentane, hexane, petroleum ether, cyclohexane, methylcyclohexane, benzene, toluene, xylene), aliphatic halohydrocarbons (methylene chloride, chloroform, di- and tetrachloroethane), nitrites (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic acid esters and lactones (ethyl or methyl acetate, valerolactone), N-substituted lactams (N-methylpyrrolidone), carboxamides (dimethylamide, dimethylformamide), acyclic ureas (dimethylimidazoline), and sulfoxides and sulfones (dimethyl sulfoxide, dimethyl sulfone, tetramethylene sulfoxide, tetramethylene sulfone) and alcohols (methanol, ethanol, propanol, butanol, ethylene glycol monomethyl ether, ethylene glycol monoethyl ether, diethylene glycol monomethyl ether) and water. The solvents can be used on their own or as a mixture of at least two solvents.

The reactions can be carried out with cooling, for example to −30° C., at room temperature or elevated temperature, for example 30 to 250° C. As a rule, equimolar amounts of the reactants are used or an excess of one reactant. The reaction products can be isolated, for example, by distillation, crystallization, chromatographic methods and/or extraction; and for purification the products can be distilled, recrystallized and/or chromatographed. The racemates or mixtures of diastereomers are separated into their pure diastereomers by recrystallization or more expediently chromatographically by means of chiral columns.

The reactions of process stages (a) to (d) are known and details are described in the examples. The reduction of process stage (c) and of ketones can be carried out catalytically using hydrogen in the presence of noble metal catalysts or more expediently using metal hydrides (LiH, NaH, NaBH$_4$, particularly LiAlH$_4$).

Suitable Grignard reagents are familiar to the person skilled in the art. Metal hydrocarbons are preferred, for example LiA$_3$, KA$_3$ or Zn(A$_3$)$_2$, or metal hydrocarbon halides, for example A$_3$MgCl, A$_3$MgBr, A$_3$MgI, A$_3$ZnCl, A$_3$ZnBr, A$_3$ZnI, A$_3$BCl$_2$, A$_3$AlCl$_2$, (A$_3$AlBr$_2$ and (A$_3$)$_2$AlBr. The Grignard reaction has been known for a long time and is described in greater detail in the examples.

A further subject of the invention is the compounds of the formula VI used as intermediates

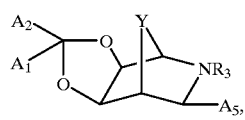

(VI)

in which

A$_1$, A$_2$, Y and R$_3$ are as defined beforehand and A$_5$ is the group —CH=O or —CO$_2$—R$_4$, and R$_4$ is C$_1$–C$_4$ alkyl, phenyl or benzyl.

The compounds of the formula I according to the invention are outstanding ligands for metal complexes of the TM8 metals of the Periodic Table of the Elements, which can be employed as catalysts or catalyst precursors, particularly in hydrogenations and transfer hydrogenations using hydrogen donors. If prochiral unsaturated compounds are employed, a high excess of optical isomers can be induced in the synthesis of organic compounds and a high chemical conversion achieved in very short reaction times.

A further subject of the invention is metal complexes of metals selected from sub-group VIII of the Periodic Table of the Elements with compounds of the formula I as ligands. In the context of the invention, the metals selected are also designated as TM8 metals.

Depending on the oxidation number and coordination number of the metal atom, the metal complexes can contain further ligands and/or anions. They can also be cationic metal complexes. Such analogous metal complexes and their preparation (in situ or as isolated compounds) are described many times in the literature [see, for example, A. Fujii et al., JACS, 118, (1996), 2521ff. and J. Takehara et al., Chem. Communication (Cambridge), and CA-A-2,239,970 and WO 98/42643].

The ligands according to the invention can be present in the metal complexes as neutral ligands or as ionic amide ligands. The metal complexes can additionally contain identical or different monodentate or bidentate, anionic or nonionic ligands. They can also be complex salts with anions of an oxygen acid or complex acid. Anions and anionic ligands serve to balance the charge of the oxidation states of the metal.

The TM8 metal can be selected from the group Fe, Ni, Co, Rh, Pd, Ir, Ru and Pt, and preferably from the group Rh, Ir and Ru, it being possible for the metal to have the oxidation states 0, 1, 2, 3 or 4.

For the compounds of the formula I, the preferences and embodiments described beforehand apply.

Monodentate nonionic ligands can be selected, for example, from the group consisting of the olefins (for example ethylene, propylene), solvating solvents (nitriles, linear or cyclic ethers, free or N-alkylated amides and lactams, amines, phosphines, alcohols, carboxylic acid esters, sulfonic acid esters), nitrogen monoxide and carbon monoxide.

Further nonionic (neutral) ligands are arenes having, for example, 6 to 24 C atoms. The arenes can be monocycles or condensed ring systems. The arenes can be substituted or unsubstituted, for example by C$_1$–C$_8$alkyl, C$_1$–C$_8$alkoxy, C$_1$–C$_4$fluoroalkyl, C$_1$–C$_8$hydroxyalkyl, hydroxyl, halogen, cyano, —CO$_2$H, —SO$_3$H, carboxy-C$_1$–C$_4$alkyl or carbamide. The arenes preferably contain 6 to 18, more preferably 6 to 14 and particularly preferably 6 to 10, C atoms. They can be substituted or unsubstituted, preferably by C$_1$–C$_6$alkyl, C$_1$–C$_6$alkoxy or halogen. Some examples of arenes are benzene, naphthalene, anthracene, fluorene, biphenyl, indan, toluene, hexamethylbenzene, 1,3,5-mesitylene and cumene.

Monodentate anionic ligands can be selected, for example, from the group consisting of hydride, halide (F, Cl, Br, I), pseudohalide (cyanide, cyanate, isocyanate) and anions of carboxylic acids, sulfonic acids, phosphonic acids (carbonate, formate, acetate, propionate, methylsulfonate, trifluoromethylsulfonate, phenylsulfonate, tosylate), allyls (allyl, 2-methallyl), and substituted or unsubstituted cyclopentadienyls (cyclopentadienyl, methylcyclopentadienyl, dimethylcyclopentadienyl, trimethylcyclopentadienyl, tetramethylcyclopentadienyl, pentamethylcyclopentadienyl, trimethylsilylcyclopentadienyl, indenyl).

Bidentate nonionic ligands can be selected, for example, from the group consisting of the linear or cyclic diolefins (for example hexadiene, cyclohexadiene, cyclooctadiene, norbornadiene), dinitriles (malononitrile), free or N-alkylated dicarboxylic acid diamides, diamines, diphosphines, diols, acetonylacetonates, dicarboxylic acid diesters, disulfonic acid diesters and the aminoalcohols.

Bidentate anionic ligands can be selected, for example, from the group consisting of the anions of dicarboxylic acids, disulfonic acids, diphosphonic acids (for example of oxalic acid, malonic acid, succinic acid, maleic acid, methylenedisulfonic acid and methylenediphosphonic acid) and bridged cyclopentadienyls [methylenebiscyclopentadienyl, methylenebis(tetramethylcyclopentadienyl), bis(cyclopentadienyidimethylsilane)].

Preferred metal complex salts are those with anions selected from the group consisting of Cl, Br, I, ClO$_4^-$, CF$_3$SO$_3^-$, HSO$_4^-$, BF$_4^-$, B(phenyl)$_4^-$, PF$_6^-$, SbCl$_6^-$, AsF$_6^-$, SbF$_6^-$ or B(3,5-CF$_3$-C$_6$H$_5$)$_4^-$.

A preferred group of metal complexes are those of the formula VII

[Ru(arene)(L)(A)] (VII), in which A is hydride or chloride, and L is a ligand of the formula I. The embodiments and preferences defined beforehand apply to the arene.

Another preferred group of metal complexes are those of the formula VIII

[Me(diene)(L)(A$_6$)] (VIII), in which Me is Rh or Ir, diene is an open-chain or cyclic diene, L is a ligand of the formula I, and A$_6$ is halide and preferably chloride, bromide or iodide. The embodiments and preferences defined beforehand apply to the diene and the ligands of the formula I. The complexes of the formula VIII are accessible by reaction of the ligand L with a metal complex of the formula [Me(diene)A$_1$)]$_2$.

A further preferred group of metal complexes are those of the formula IX

[Me$_1$Cp(L)A$_7$] (IX), in which Me$_1$ is Rh, Ir or Ru, A$_7$ is hydride or halide, preferably chloride, L is a ligand of the formula I, and Cp is a substituted or unsubstituted cyclopentadienyl or indenyl. The embodiments and preferences defined beforehand apply to the ligands of the formula I and cyclopentadienyis and indenyls. The complexes of the formula IX are accessible by reaction of the ligand L with a metal complex of the formula [Me$_1$Cp(A$_7$)]$_2$.

The metal complexes according to the invention are prepared according to methods known in the literature (see also CA-A-2,239,970 and WO 98/42643).

The metal complexes according to the invention are homogeneous catalysts or catalyst precursors which can be activated under the reaction conditions and can be employed, for example, for hydrogenations of unsaturated organic compounds.

Preferably, the metal complexes are used for the asymmetric hydrogenation of prochiral compounds having carbon/carbon or carbon/heteroatom multiple, in particular double, bonds. The metal complexes are particularly suitable for transfer hydrogenations using hydrogen donors. Hydrogenations of this type using soluble homogeneous metal complexes are described, for example, in Pure and Appl. Chem., Vol. 68, No. 1, pp. 131–138 (1996).

The invention therefore further relates to the use of the metal complexes according to the invention as homogeneous catalysts for hydrogenation, preferably transfer hydrogenations using hydrogen donors, of prochiral compounds having carbon/carbon or carbon/heteroatom multiple bonds, in particular carbon/heteroatom double bonds.

A further aspect of the invention is a process for asymmetric hydrogenation using hydrogen, or for transfer hydrogenation using hydrogen donors, of prochiral compounds having carbon/carbon or carbon/heteroatom multiple bonds, in particular carbon/heteroatom double bonds, wherein the compounds are reacted at low to elevated temperatures in the presence of catalytic amounts of a metal complex according to the invention.

Preferred prochiral, unsaturated compounds to be hydrogenated can contain one or more, identical or different groups C=C, C=N and/or C=O, in open-chain or cyclic organic compounds, it being possible for the groups C=C, C=N and/or C=O to be part of a ring system or being exocyclic groups. The prochiral unsaturated compounds can be alkenes, cycloalkenes, heterocycloalkenes, and open-chain or cyclic ketones, ketimines and ketohydrazones. They can have, for example, the formula X

R$_5$R$_6$C=D (X), in which R$_5$ and R$_6$ are selected such that the compound is prochiral, and independently of one another are an open-chain or cyclic hydrocarbon radical or heterohydrocarbon radical having heteroatoms selected from the group consisting of O, S and N, which contain 1 to 30 and preferably 1 to 20 C atoms;

D is O or a radical of the formula CR$_7$R$_8$ or NR$_9$;

R$_7$ and R$_8$ independently of one another have the same meaning as R$_5$ and R$_6$, R$_9$ is hydrogen, C$_1$–C$_{12}$alkyl, C$_1$–C$_{12}$alkoxy, C$_3$–C$_{12}$cycloalkyl, C$_3$–C$_{12}$cycloalkyl-C$_1$–C$_6$alkyl, C$_3$–C$_{11}$heterocycloalkyl, C$_3$–C$_{11}$heterocycloalkyl-C$_1$–C$_6$alkyl, C$_6$–C$_{14}$aryl, C$_5$–C$_{13}$heteroaryl, C$_7$–C$_{16}$aralkyl or C$_6$–C$_{14}$heteroaralkyl, R$_5$ and R$_6$, together with the C atom to which they are bonded, form a hydrocarbon ring or heterohydrocarbon ring having 3 to 12 ring members;

R$_5$ and R$_7$ each, together with the C=C group to which they are bonded, forms a hydrocarbon ring or heterohydrocarbon ring having 3 to 12 ring members;

R$_5$ and R$_9$ each, together with the C=N group to which they are bonded, forms a hydrocarbon ring or heterohydrocarbon ring having 3 to 12 ring members; the heteroatoms in the heterocyclic rings are selected from the group consisting of O, S and N;

and R$_5$, R$_6$, R$_7$, R$_8$ and R$_9$ are substituted or unsubstituted by C$_1$–C$_6$alkyl, C$_1$–C$_6$alkoxy, cyclohexyl, C$_6$–C$_{10}$aryl, C$_7$–C$_{12}$aralkyl, C$_1$–C$_4$alkyl-C$_6$–C$_{10}$aryl, C$_1$–C$_4$alkoxy-C$_6$–C$_{10}$aryl, C$_1$–C$_4$-alkyl-C$_7$–C$_{12}$aralkyl, C$_1$–C$_4$alkoxy-C$_7$–C$_{12}$aralkyl, —OH, —CO—OR$_{10}$, —CO—NR$_{11}$R$_{12}$ or —NR$_{11}$R$_{12}$, in which R$_{10}$ is H, an alkali metal, C$_1$–C$_6$alkyl, cyclohexyl, phenyl or benzyl, and R$_{11}$ and R$_{12}$ independently of one another are hydrogen, C$_1$–C$_6$alkyl, cyclohexyl, phenyl or benzyl, or R$_{11}$ and R$_{12}$ together are tetramethylene, pentamethylene or 3-oxapentylene.

Examples and preferences for substituents have been mentioned beforehand.

R$_7$ and R$_8$ can be, for example, C$_1$–C$_{20}$alkyl and preferably C$_1$–C$_{12}$alkyl, C$_1$–C$_{20}$heteroalkyl and preferably C$_1$–C$_{12}$heteroalkyl having heteroatoms selected from the group consisting of O, S and N, C$_3$–C$_{12}$cycloalkyl and preferably C$_4$–C$_8$cycloalkyl, C-bonded C$_3$–C$_{11}$heterocycloalkyl and preferably C$_4$–C$_8$heterocycloalkyl having heteroatoms selected from the group consisting of O, S and N, C$_3$–C$_{12}$cycloalkyl-C$_1$–C$_6$alkyl and preferably C$_4$–C$_8$cycloalkyl-C$_1$–C$_6$alkyl, C$_3$–C$_{11}$heterocycloalkyl-C$_1$–C$_6$alkyl and preferably C$_4$–C$_8$heterocycloalkyl-C$_1$–C$_6$alkyl having heteroatoms selected from the group consisting of O, S and N, C$_6$–C$_{14}$aryl and preferably C$_6$–C$_{10}$aryl, C$_5$–C$_{13}$heteroaryl and preferably C$_5$–C$_9$heteroaryl having heteroatoms selected from the group consisting of O, S and N, C$_7$–C$_{15}$aralkyl and preferably C$_7$–C$_{11}$aralkyl, C$_6$–C$_{12}$heteroaralkyl and preferably C$_6$–C$_{10}$heteroaralkyl having heteroatoms selected from the group consisting of O, S and N.

If $R_5$ and $R_6$, $R_5$ and $R_7$, or $R_5$ and $R_9$ each, together with the group to which they are bonded, form a hydrocarbon ring or heterohydrocarbon ring, the ring preferably contains 4 to 8 ring members. The heterohydrocarbon ring can contain, for example, 1 to 3, and preferably one or two, heteroatoms.

In the formula X, D is preferably the radical $NR_9$, and particularly preferably O.

$R_9$ is preferably hydrogen, $C_1$–$C_6$alkyl, $C_1$–$C_6$alkoxy, $C_4$–$C_8$cycloalkyl, $C_4$–$C_8$cycloalkyl-$C_1$–$C_4$alkyl, $C_4$–$C_{10}$heterocycloalkyl, $C_4$–$C_{10}$heterocycloalkyl-$C_1$–$C_4$alkyl, $C_6$–$C_{10}$aryl, $C_5$–$C_9$heteroaryl, $C_7$–$C_{12}$aralkyl or $C_5$–$C_{13}$heteroaralkyl.

Some examples of prochiral ketones are acetophenone, 4-methoxyacetophenone, 4-tri-fluoromethylacetophenone, 4-nitroacetophenone, 2-chloroacetophenone, corresponding acetophenone benzylimines, substituted or unsubstituted benzocyclohexanone or benzocyclopentanone, and imines from the group consisting of substituted or unsubstituted tetrahydroquinoline, tetrahydropyridine and dihydropyrrole.

Hydrogen donors are, for example, primary and secondary alcohols, primary and secondary amines, carboxylic acid esters, carboxylic acids and their ammonium salts, readily dehydrogenable hydrocarbons and reducing agents. The hydrogen donors are used in at least equimolar amounts or an excess, based on the compound to be hydrogenated. The excess can be up to 5 mol and more, particularly if suitable hydrogen donors simultaneously serve as solvents. Hydrogen donors can be employed as a mixture with additional hydrogen.

The primary and secondary alcohols preferably contain 1 to 10 C atoms, particularly preferably 2 to 6 C atoms and especially preferably 3 or 4 C atoms. Some examples are methanol, ethanol, n- and i-propanol, n- and i-butanol, 1-, 2- or 3-pentanol, 1-, 2- or 3-hexanol, cyclopentanol, cyclohexanol, benzyl alcohol and menthol. Secondary alcohols are preferred, particularly i-propanol and i-butanol.

The primary and secondary amines can contain, for example, 1 to 20 C atoms, preferably 2 to 16 C atoms and particularly preferably 3 to 12 C atoms. Some examples are ethylamine, n- and i-propylamine, n- and i-butylamine, pentylamine, hexylamine, benzylamine, piperidine, morpholine, cyclohexylamine, diethylamine, di-n- or -i-propylamine, di-n- or -i-butylamine, dipentylamine and dihexylamine. Primary amines are preferred, particularly primary amines having a branched alkyl group, for example i-propylamine and i-butylamine.

The carboxylic acids are preferably aliphatic or cycloaliphatic carboxylic acids which contain, for example, 1 to 10 C atoms, and preferably 1 to 4 C atoms. They can be substituted by hydroxyl groups, particularly in the βposition relative to the carboxyl group. Some examples are formic acid, lactic acid and ascorbic acid. Carboxylic acid esters can be derived from the carboxylic acids mentioned beforehand and contain, for example, a $C_1$–$C_{20}$alkyl group, preferably $C_1$–$C_4$alkyl group, in the ester group.

The ammonium salts can be derived from the carboxylic acids and primary, secondary, tertiary or quaternary ammonium mentioned beforehand. The ammonium can contain, for example, 1 to 20, preferably 2 to 16, and particularly preferably 3 to 12, C atoms. Tri($C_1$–$C_4$alkyl)ammonium is particularly suitable. Some examples of ammonium are methylammonium, dimethylammonium, trimethylammonium, ethylammonium, diethylammonium, triethylammonium, methylethylammonium, i-propyidiethylamine, di-i-propylethylamine. Trialkylammonium formates are particularly preferable, particularly triethyl formate. The molar ratio of carboxylic acid to amine in the reaction mixture is in general approximately 5 to 2.

Readily dehydrogenable hydrocarbons are, for example, those which are prone to aromatization or formation of conjugated systems. Some examples are cyclohexadiene, cyclohexene, tetralin, dihydrofuran and terpenes.

Suitable reducing agents are, for example, hydrazine and hydroxylamine.

Low to elevated temperature in the context of the invention can be, for example, from −20 to 150° C., preferably from −10 to 100° C., and particularly preferably from 10 to 80° C. The optical yields are in general better at lower temperature than at higher temperatures. In hydrogenations, the hydrogen pressure can be, for example, from $10^5$ to $2 \times 10^7$ Pa (Pascal). The transfer hydrogenation is preferably carried out at normal pressure or slight overpressure.

Catalysts are preferably used in amounts from 0.0001 to 10 mol%, particularly preferably 0.001 to 10 mol%, and especially preferably 0.01 to 5 mol%, based on the compound to be hydrogenated. The molar ratio of substrate to catalyst can be, for example, from 10 to 10 000, preferably 50 to 5 000 and particularly preferably 100 to 3 000.

The reaction can be carried out without solvent or in the presence of inert solvents. Solvents are generally known and their choice depends mainly on the solubility of substrate and metal complexes. Suitable solvents have been mentioned beforehand.

The reaction can be carried out in the presence of bases. Suitable bases are, for example, alkali metal and alkaline earth metal bases [LiOH, NaOH, KOH, Mg(OH)$_2$ and Ca(OH)$_2$], alkali metal alkoxides of $C_1$–$C_6$alkanols (lithium, sodium, potassium or cesium methoxide, ethoxide, n- and i-propoxide, n-, i- and t-butoxide), alkali metal carbonates (Li$_2$CO$_3$, Na$_2$CO$_3$, K$_2$CO$_3$, KHCO$_3$) and alkali metal carboxylates of $C_1$–$C_6$carboxylic acids (formates, acetates, propionates and butyrates). The molar ratio of catalyst metal to the base is, for example, from 1:1 to 1:4, preferably 1:1 to 1:2.

The metal complexes used as catalysts can be added as separately prepared isolated compounds, or formed in situ before the reaction and then mixed with the substrate to be hydrogenated. It can be advantageous in the case of hydrogenation using isolated metal complex additionally to add ligands, or in the case of the in situ preparation to employ an excess of the ligands. The excess can be, for example, 1 to 10 and preferably 1 to 5 mol, based on the metal compound used for preparation.

The hydrogenation can be carried out continuously or batchwise in various types of reactor. Preferred reactors are those which allow comparatively favorable mixing and good heat dissipation, for example loop reactors. This type of reactor has especially proven suitable when using small amounts of catalyst.

A further subject of the invention is the use of the metal complexes according to the invention as homogeneous catalysts for the hydrogenation, preferably transfer hydrogenation using hydrogen donors, of prochiral compounds having carbon/carbon or carbon/heteroatom multiple bonds, in particular carbon/heteroatom double bonds.

Another subject of the invention is a kit, comprising, in separate vessels, as component (a) a metal complex, a metal complex salt or a metal compound from the group consisting of the TM8 metals which are able to form a catalyst with the ligand, and as component (b) a ligand according to the invention. The kit is particularly suitable for the in situ preparation of catalysts. The components can be dissolved in solvents. Suitable solvents, metal complexes, metal complex salts and metal compounds have been mentioned beforehand. The molar ratio of component (a) to component (b) can be adjusted to 1 to 1 to 10, preferably 1 to 1 to 5.

The hydrogenated organic compounds which can be prepared according to the invention are active substances or intermediates for the preparation of such substances, in particular in the area of the preparation of pharmaceuticals and agrochemicals. Thus o,o-dialkylarylketamine derivatives, for example, in particular those having alkyl and/or alkoxyalkyl groups, act as fungicides, particularly as herbicides. The derivatives can be amine salts, acid amides, e.g. of chloroacetic acid, tertiary amines and ammonium salts (see, for example, EP-A-0 077 755 and EP-A-0 115 470).

The following examples illustrate the invention.

A) Preparation of Intermediates

EXAMPLE A1

Methyl (1S,2R,6S,7R,9R)-4,4-dimethyl-8[(S)-1-phenylethyl)]-3,5-dioxa-8-azatricyclo[5.2.1.0.$^{0,0}$] decane-9-carboxylate (100)

a) 6.6 g (26 mmol) of methyl N-(S)-phenylethyl-2-azanorbornene-3-carboxylate are dissolved at room temperature in a mixture of 72 ml of tertiary butanol and 9.8 ml of water. 40 ml of NMO (60 percent strength aqueous solution, 230 mmol) and after this OsO$_4$ (0.2 g, 0.6 mmol) are then added. The mixture is stirred overnight and then treated with an aqueous solution of NaS$_2$O$_5$. After removal of the solvent in vacuo, the residue is washed with 40 ml of aqueous NaCl solution and three times 100 ml of methylene chloride. The solution is dried over MgSO$_4$, the solvent is evaporated and pure methyl (1S,2R,4S,5R,6S)-5,6-dihydroxy-2-((S)-1 -phenylethyl)-2-azabicyclo[2.2.1]heptane-3-carboxylate (101) is obtained in quantitative yield, which is reused directly in the following stage.

$^1$H NMR: δ1.4 (3H, d, J=6.4 Hz), 1.77 (1H, d, J=10.8 Hz), 1.92 (1H, d, J=10.8 Hz), 2.21 (1H, bs) 2.44 (1H, bs), 3.45 (3H, s), 3.54 (1H, q, J=6.4 Hz), 3.55 (1H, bs), 3.79 (1H, d, J=5.2), 4.25 (1H, d, J=5.2) and 7.12–7.27 (5H, m); $^{13}$C NMR: δ22.2, 29.6, 48.8, 51.5, 60.1, 61.6, 65.6, 67.2, 73.2, 127.4, 127.9, 128.0, 143.8 and 173.9.

b) The compound 101 (7.4 g, 26 mmol) is dissolved in methanol and 4.9 g (26 mmol) of p-toluenesulfonic acid and 7.9 ml (65 mmol) of 2,2-dimethoxypropane are added. The reaction mixture is warmed to 45° C. and stirred overnight. The solvent is then removed under reduced pressure and the residue is washed with 50 ml of 2 M NaOH and three times 100 ml of methylene chloride. After drying over MgSO$_4$ and evaporating the solvent, purification is carried out by means of flash chromatography (deactivated silica). The pure compound (100) is obtained in 89% yield (8.4 g). Analytical data:

[α]$_D^{30°\ C.}$=+1.9 (c 1.0, CH$_2$Cl$_2$); melting point: 82 83° C.; IR (CH$_2$Cl$_2$, cm$^{-1}$): 2976, 1746, 1491, 1455 and 1375; $^1$H NMR: δ1.33 (3H, s), 1.46 (3H, d, J=6.4 Hz), 1.46 (3H, s), 1.74 (1H, d, J=10.4 Hz ), 1.91 (1H, d, J=10.4 Hz), 2.34 (1H, s), 2.42 (1H, s), 3.25 (3H, s), 3.60 (1H, q, J=6.4 Hz), 3.71 (1H, s), 4.15 (1H, d, J=5.6 Hz), 4.55 (1H, d, J=5.6 Hz) and 7.18–7.23 (5H, m); $^{13}$C NMR: δ22.4, 24.3, 25.4, 29.3, 45.9, 51.4, 59.0, 60.1, 64.2, 75.6, 80.5, 109.6, 127.4, 127.8, 128.0, 144.0 and 173.6; MS (EI) m/z (relative intensity) 276 (M$^+$, <1%), 196 (14), 195 (100), 105 (12) and 79 (12).

EXAMPLE A2

Methyl (1S, 2R, 6S, 7R, 9R)-4,4-dimethyl-3,5-dioxa-8-azatricyclo[5.2.1.0$^{0,0}$]-decane-9-carboxylate (102)

8.4 g (25 mmol) of the compound (100) are dissolved in 50 ml of methanol and 2.5 g (30% by weight) of dried Pd(OH)$_2$ are then added. Hydrogen is injected, and the mixture is warmed to 50° C. and stirred overnight. The reaction product is then filtered through Celite, the filtrate is dried over MgSO$_4$ and the solvent is evaporated. The pure compound (102) is obtained in quantitative yield (5.8 g).

$^1$H NMR: δ1.25 (3H, d, J=10.8 Hz), 1.26 (3H, s), 1.71 (1H, d, J=10.8 Hz), 2.04 (1H, bs) 2.63 (1H, bs), 3.05 (1H, bs) 3.41 (1H, bs), 3.72 (3H, s), 4.07 (1H, d, J=5.6 Hz) and 4.07 (1H, d, J=5.6 Hz); $^{13}$C NMR: δ24.2, 25.5, 28.8, 44.4, 52.5, 57.24, 57.47, 80.6, 81.6, 110.1 and 174.2.

EXAMPLE A3

Methyl (1S,2R,6S,7R,9R)-4,4-diethyl-8[(S)-1-phenylethyl)]-3,5-dioxa-8-azatricyclo[5.2.1.0.$^{0,0}$] decane-9-carboxylate (103)

Methyl (1S,2R,4S,5R,6S)-5,6-dihydroxy-2-((S)-1-phenylethyl)-2-azabicyclo[2.2.1]heptane-3-carboxylate (103) is prepared according to example A1(a). 0.7 g (2.4 mmol) of compound (103) is dissolved in 50 ml of methanol, and 0.46 g (2.4 mmol) of p-toluenesulfonic acid and 0.6 ml (9.6 mmol) of acetone are then added successively. The mixture is heated to reflux overnight. The solvent is then evaporated, the residue is washed with 5 ml of 2 M NaOH and three times 20 ml of methylene chloride. The solution is dried over MgSO$_4$, the methylene chloride is evaporated and the residue is purified by means of flash chromatography. 0.59 g (68%) of the compound 103 is obtained. Analytical data: [α]$_D^{24°\ C.}$=+0.4 (c 1.9, CH$_2$Cl$_2$); melting point: 82 to 83° C.; IR (CH$_2$Cl$_2$, cm$^{-1}$): 2971, 1743, 1492, 1458 and 1379; $^1$H NMR: δ0.90 (3H, t, J=7.6 Hz), 0.95 (3H, t, J=7.6 Hz), 1.46 (3H, d, J=6.4 Hz), 1.59 (2H, q, J=7.6 Hz), 1.70 (2H, q, J=7.6 Hz), 1.81 (1H, d, J=10.4 Hz), 1.88 (1H, d, J=10.4 Hz), 2.37 (1H, s), 2.41 (1H, s), 3.25 (3H, s), 3.58 (1H, q, J=6.4 Hz), 3.74 (1H, s) 4.12 (1H, d, J=5.6 Hz), 4.51 (1H, d, J=5.6 Hz) and 7.18 to 7.26 (5H, m); $^{13}$C NMR: δ8.2, 8.2, 22.4, 27.3, 27.9, 29.4, 46.0, 51.5, 59.0, 60.1, 64.3, 75.5, 80.4, 113.7, 127.4, 127.8, 128.0, 144.0 and 173.6; MS (EI) m/z (relative intensity) 358 (M$^-$, 20%), 329 (32), 300 (18), 229 (100), 225 (43), 126 (60), 105 (79) and 79 (17).

EXAMPLE A4

Methyl (1S, 2R, 6S, 7R, 9R)-4,4-diethyl-3,5-dioxa-8-azatricyclo[5.2.1.0$^{0,0}$]-decane-9-carboxylate (104)

The debenzylation of the compound (103) is carried out according to example A2 and the title compound (104) is obtained in quantitative yield. Analytical data: $^1$H NMR: δ0.86 (3H, t, J=8 Hz), 0.93 (3H, t, J=8.0 Hz), 1.27 (1H, d, J=10.8 Hz), 1.55 (2H, q, J=8.0 Hz), 1.66 (2H, q, J=8.0 Hz), 1.81 (1H, d, J=10.8 Hz), 2.69 (1H, s), 3.08 (1H, s), 3.48 (1H, s), 3.74 (3H, s), 4.09 (1H, d, J=5.2 Hz) and 4.17 (1H, d, J=5.2 Hz); $^{13}$C NMR: δ8.0, 8.6 27.3 27.8 28.9, 44.4, 52.4, 57.2, 57.4, 80.4, 81.4, 114.1 and 174.1.

EXAMPLE A5

Methyl (1S, 2R, 6S, 7R, 9R)-4-methyl-4-phenyl-3,5-dioxa-8-azatricyclo-[5.2.1.0$^{0,0}$]decane-9-carboxylate (105)

a) The reaction of 0.70 g (2.4 mmol) of the compound 101 with 0.80 ml (6.8 mmol) of acetophenone is carried out according to example A3 and 0.77 g (70%) of the compound methyl (1S,2R,4S,6S, R,7R,9R)-4-methyl-4-phenyl-8-[(S)-1-phenylethyl)]-3,5-dioxa-8-azatricyclo-[5.2.1.0$^{0,0}$]decane-9-carboxylate (106) is obtained. Analytical data:

[α]$_D^{24°C.}$=+0.4 (c 1.9, CH$_2$Cl$_2$); melting point: 82 to 83° C.; IR (CH$_2$Cl$_2$, cm$^{-1}$): 2971, 1743, 1492, 1458 and 1379; $^1$H NMR: δ0.90 (3H, t, J=7.6 Hz), 0.95 (3H, t, J=7.6 Hz), 1.46 (3H, d, J=6.4 Hz), 1.59 (2H, q, J=7.6 Hz), 1.70 (2H, q, J=7.6 Hz), 1.81 (1H, d, J=10.4 Hz ), 1.88 (1H, d, J=10.4 Hz), 2.37 (1H, s), 2.41 (1H, s), 3.25 (3H, s), 3.58 (1H, q, J=6.4 Hz), 3.74 (1H, s,) 4.12 (1H, d, J=5.6 Hz), 4.51 (1H, d, J=5.6 Hz) and 7.18 to 7.26 (5H, m); $^{13}$C NMR: δ8.2 22.4, 27.3, 27.9, 29.4, 46.0, 51.5, 59.0, 60.1, 64.3, 75.5, 80.4, 113.7, 127.4, 127.8, 128.0, 144.0 and 173.6; MS (El) m/z (relative intensity): 358 (M$^-$, 20%), 329 (32), 300 (18), 229 (100), 225 (43), 126 (60), 105 (79) and 79 (17).

b) The debenzylation of the compound (106) is carried out according to example A2 and the title compound (105) is obtained in quantitative yield. Analytical data: $^1$H NMR: δ0.86 (3H, t, J=8 Hz), 0.93 (3H, t, J=8.0 Hz), 1.27 (1H, d, J=10.8 Hz), 1.55 (2H, q, J=8.0 Hz), 1.66 (2H, q, J=8.0 Hz), 1.81 (1H, d, J=10.8 Hz), 2.69 (1H, s), 3.08 (1H, s), 3.48 (1H, s) 3.74 (3H, s), 4.09 (1H, d, J=5.2 Hz) and 4.17 (1H, d, J=5.2 Hz); $^{13}$C NMR: δ8.0, 8.6 27.3, 27.8, 28.9, 44.4, 52.4, 57.2, 57.4, 80.4, 81.4, 114.1 and 174.1.

EXAMPLE A6

(1S, 2R, 6S, 7R, 9R)-4-4-Dimethyl-8-[(S)-2-phenylethyl]-3,5-dioxa-8-azatricyclo[5.2.1.0$^{0,0}$]decane-9-carbaldehyde (107)

a) 11 g (35 mmol) of compound 100 are dissolved in 80 ml of tetrahydrofuran and a suspension of 1.3 g (35 mmol) of LiAlH$_4$ in tetrahydrofuran is added dropwise at 0° C. The reaction mixture is stirred at 0° C. for one hour and then treated successively with 1.3 ml of water, 1.3 ml of 1 M NaOH and 3.9 ml of water. It is filtered, the filtrate is dried over MgSO$_4$ and the solvent is removed in vacuo. The (1S, 2R, 6S, 7R, 9R)-4-4-dimethyl-8-[(S)-2-phenylethyl]-3,5-dioxa-8-azatricyclo[5.2.1.0$^{0,0}$]decane-9-methanol (108) obtained in 94% yield (10 g) is used directly in stage b).

b) 4.2 ml of dimethyl sulfoxide (79 mmol) are added at −78° C. in the course of 10 minutes to 3.1 ml (36 mmol) of oxalyl chloride in 200 ml of methylene chloride and the mixture is stirred for 15 minutes. A solution of 10 g of compound (108) in methylene chloride is then added dropwise in the course of 10 minutes, the mixture is stirred for 15 minutes and 16 ml (120 mmol) of triethylamine are then added in the course of 10 minutes. The reaction mixture is then allowed to warm to room temperature, is washed with 100 ml of concentrated NaCl solution and three times 200 ml of methylene chloride, dried over MgSO$_4$ and the methylene chloride is then evaporated. After the purification of the residue by means of flash chromatography, 8.9 g (89%) of the compound 107 are obtained. Analytical data: [α]$_D^+$=+10.2 (c 2.3, CH$_2$Cl$_2$); IR (cm$^{-1}$) 2980, 1723, 1382 and 1207; $^1$H NMR: δ1.32 (3H, s), 1.43 (3H, s), 1.45 (1H, m), 1.47 (3H, d, J=6.4 Hz), 1.75 (1H, d, J=10.8 Hz), 2.26 (1H, d, J=2.8 Hz), 2.44 (1H, s), 3.58 (1H, q, J=6.6 Hz), 3.72 (1H, s), 4.16 (1H, d, J=5.4 Hz), 4.56 (1H, d, J=5.4 Hz), 7.12–7.30 (5 H, m) and 8.97 (1H,s); $^{13}$C NMR: δ22.0, 24.1, 25.3, 29.6, 44.8, 59.2, 59.7, 69.6, 75.8, 80.2, 109.4, 127.5, 127.8, 128.4, 144.0 and 203.2; MS (El) m/z (relative intensity); 259 (M$^+$, 6%), 200 (100), 186 (11), 172 (40) and 91 (41).

B) Preparation of Ligands

EXAMPLE B1

[(1S, 2R, 6S, 7R, 9R)-4,4-Dimethyl-3,5-dioxa-8-azatricyclo[5.2.1.0$^{0,0}$]decane-9]methanol (108)

A solution of 5.8 g (25 mmol) of compound (102) in tetrahydrofuran is added dropwise at 0° C. to a suspension of 6.6 g (0.18 mol) of LiAlH$_4$ in tetrahydrofuran. The cooling bath is removed and the mixture is allowed to warm to room temperature. After 25 minutes, 6.6 ml of water, 6.6 ml of 1 M NaOH and 20 ml of water are slowly added successively. The mixture is then filtered, dried over MgSO$_4$ and the solvent is removed in vacuo. The residue is taken up in a mixture of ethyl acetate and pentane and crystallized. 4.7 g (90%) of the compound (108) are obtained. Analytical data: [α]$_D^{24°C.}$=−2.9 (c 0.5, CH$_2$Cl$_2$); melting point: 98 to 101° C; IR (CH$_2$Cl$_2$, cm$^{-1}$): 3357, 2974, 1458, and 1168; $^1$H NMR: δ1.31 (3H, s), 1.44 (1H, d, J=10.4 Hz), 1.46 (3H, s), 1.70 (1H, d, J=10.4 Hz), 2.28 (1H, s), 2.61 (1H, dd, J=8.0 and 5.6 Hz), 3.28 (1H, dd, J=8.0 and 10.4 Hz), 3.35 (1H, bs), 3.50 (1H, dd, J=10.4 and 6.0 Hz), 4.00 (1H, d, J=5.6 Hz) and 4.15 (1H, d, J=5.6 Hz); $^{13}$C NMR: δ24.2, 25.5 27.9, 42.0, 55.6, 57.0, 65.1, 80.8, 82.5 and 109.6; MS (El) m/z (relative intensity): 276 (M$^+$, <1%), 196 (14), 195 (100), 105 (12) and 79 (12).

EXAMPLE B2

[(1S,2R,6S,7R,9R)-4,4-Diethyl-3,5-dioxa-8-azatricyclo[5.2.1.0$^{0,0}$]decane-9]-methanol (109)

5.8 g (25 mmol) of the compound 104 are reduced according to example B1. The compound (109) is obtained in 68% yield. Analytical data: [α]$_D^{24°C.}$=−23.5 (c 0.4, CH$_2$Cl$_2$); melting point; 53 to 54° C.; IR (CH$_2$Cl$_2$, cm$^{-1}$): 3360, 2975, 1458, and 1169; $^1$H NMR: δ0.80 (3H, t, J=7.6 Hz), 0.89 (3H, t, J=7.6 Hz), 1.32 (1H, d, J=10.4 Hz), 1.50 (2H, q, J=7.6 Hz), 1.60 (2H, q, J=7.6 Hz), 1.68 (1H, d, J=10.4 Hz), 2.24 (1H, s), 2.49 (1H, dd, J=8.0 and 5.4 Hz), 3.22 (1H, dd, J=8.0 and 10.2 Hz), 3.27 (1H, bs), 3.39 (1H, dd, J=10.2 and 5.4 Hz), 3.89 (1H, d, J=5.2 Hz) and 4.02 (1H, d, J=5.2 Hz); $^{13}$C NMR: δ8.0, 8.6, 27.3, 27.9, 28.0, 41.8, 56.1, 60.0, 64.9, 80.6, 82.0, and 113.6; MS (EI) m/z (relative intensity): 276 (M$^+$, <1%), 196 (14), 195 (100), 105 (12) and 79 (12).

EXAMPLE B3

[(1S,2R,4S,6S,7R,9R)-4-Methyl-4-phenyl-3,5-dioxa-8-azatricyclo[5.2.1.0$^{0,0}$]-decane-9]methanol (110)

5.8 g (25 mmol) of the compound 104 are reduced according to example B1. The compound (110) is obtained in 67% yield. Analytical data: [α]$_D^{25}$=+71.4 (c 1.4, CH$_2$Cl$_2$); IR (KBr, cm$^{-1}$): 2927, 1138 and 1043; $^1$H NMR: δ1.35 (1H, d, J=10.8 Hz), 1.56 (1H, m), 1.58 (3H, s), 2.34 (1H, s), 2.62 (1H, dd, J=8.0 Hz, J=5.6 Hz), 3.26 (1H, dd, J=10.8 Hz, J=8.0 Hz), 3.39 (1H, s), 3.47 (1H, dd, J=10.8 Hz, J=5.6 Hz), 4.15 (1H, d, J=5.2 Hz), 4.31 (1H, d, J=5.2 Hz) and 7.25–7.60 (5 H, m); $^{13}$C NMR: δ25.4, 28.0, 41.8, 56.0, 56.9, 64.9, 80.9, 82.1, 110.0, 124.7, 125.2, 127.9, 128.1, and 141.5; MS (El) m/z (relative intensity): 259 (M$^+$, 6), 200 (100), 186 (11), 172 (40) and 91 (41).

EXAMPLE B4

(R)-1-[(1S, 2R, 6S, 7R, 9R)-4,4-Dimethyl-3,5-dioxa-8-azatricyclo[5.2.1.0$^{0,0}$]dec-9-yl]ethanol (111)

a) A suspension of 22 g (88 mmol) of CeCl$_3$ in diethyl ether is initially introduced and a suspension of methylMgI (29 ml, 3 M in diethyl ether) is added at −78° C. The mixture is stirred and 8.9 g (29 mmol) of compound (101) dissolved in diethyl ether are added. Stirring is continued and the mixture is allowed to warm to room temperature overnight. The diethyl ether is removed in vacuo and the residue is taken up using 400 ml of methylene chloride and washed with 200 ml of water and three times 400 ml of methylene chloride. After drying over MgSO$_4$ and evaporating the solvent, 9.3 g (98%) of crude product (diastereomeric mixture R:S=95:5) are obtained, which is used directly for the oxidation.

b) The crude product is oxidized and worked up according to example A6b. 1-[(1S, 2R, 6S, 7R, 9R)-4,4-dimethyl-8-[(S)-1-phenylethyl]-3,5-dioxa-8-azatricyclo[5.2.0$^{0,0}$]dec-9-yl]-ethanone (112) is obtained in 86% yield. Analytical data: $[\alpha]_D^{25}$=+3.8 (c 0.8, CH$_2$Cl$_2$); melting point: 98 to 99° C.; IR (KBr, cm$^{-1}$): 2978, 1702, 1382 and 1206; $^1$H NMR: δ1.35 (3H, s), 1.45 (3H, s), 1.47 (3H, d, J=6.8 Hz), 1.53 (3H, s), 1.68 to 1.77 (2H, m), 2.24 (1H, s), 3.50 (1H, s), 3.56 (1H, q, J=6.6 Hz), 3.74 (1H, s), 4.20 (1H, d, J=5.6 Hz), 4.59 (1H, d, J=5.6 Hz) and 7.15 to 7.28 (5 H, m); $^{13}$C NMR: δ21.8, 24.3, 25.4, 27.3, 28.9, 45.3, 59.4, 60.0, 70.5, 75.6, 80.9, 109.7, 127.7, 128.2, 128.3, 144.0, and 209.3; MS (El) m/z (relative intensity): 259 (M$^+$, 6), 200 (100), 186 (11), 172 (40) and 91 (41).

c) The compound 112 is reduced according to example B1. The 1:1 mixture of the S and R diastereomers is separated by means of flash chromatography (ethyl acetate/pentane 1:4, deactivated silica column). (S)-1-[(1S, 2R, 6S, 7R, 9R)-4,4-Dimethyl-8-[(S)-1-phenylethyl]-3,5-dioxa-8-azatricyclo[5.2.0$^{0,0}$]dec-9-yl]ethanol (Rf=0.33) is obtained in 45% yield and (R)-1-[(1S, 2R, 6S, 7R, 9R)-4,4-dimethyl-8-[(S)-1-phenylethyl]-3,5-dioxa-8-azatricyclo[5.2.0$^{0,0}$]-dec-9-yl]ethanol (Rf=0.2) is obtained in 46% yield.

Analytical data of S diastereomer: $^1$H NMR: δ0.80 (3H, d, J=6.6 Hz), 1.35 (3H, s), 1.46 (3H, s), 1.48 (3H, d, J=6.6 Hz), 1.61 (1H, d, J=10.4 Hz), 1.69 (1H, d, J=10.4 Hz), 1.72 (1H, d, J=3.6 Hz), 2.29 (1H,m), 2.41 (1H, s), 3.61 (1H, q, J=6.4 Hz), 3.66 (1H, s) 4.08 (1H, d, J=5.8 Hz), 4.58 (1H, d, J=5.8 Hz), and 7.20 to 7.38 (5 H, m); $^{13}$C NMR: δ18.0, 22.6, 24.4, 25.5, 29.6, 40.3, 59.8, 60.2, 65.3, 67.6, 76.0, 81.2, 109.3, 127.0, 127.8, 128.7 and 145.6.

Analytical data of R diastereomer: $^1$H NMR: δ0.56 (3H, d, J=6.6 Hz), 1.34 (3H, s), 1.45 (3H, s), 1.47 (3H, d, J=6.6 Hz), 1.51 (1H, d, J=10.4 Hz), 1.67 (1H, d, J=10.4 Hz). 1.88 (1H, d, J=4.4 Hz), 2.23 (1H, s), 2.83 (1H, m), 3.58 (1H, q, J=6.4 Hz), 3.61 (1H, s), 4.15 (1H, d, J=5.4 Hz), 4.58 (1H, d, J=5.4 Hz), and 7.20 to 7.35 (5 H, m); $^{13}$C NMR: δ19.9, 22.4, 24.3, 25.5, 29.0, 44.4, 59.9, 60.2, 67.4, 68.3, 76.0, 80.3, 109.3, 127.8, 128.0, 128.5, and 145.3.

d) The debenzylation of the R-methyl diastereomer is carried out according to example A2 and the title compound (111) is obtained in quantitative yield. Analytical data: $[\alpha]_D^{25}$=−19.2 (c 0.8, CH$_2$Cl$_2$); melting point: 53° C.; IR (KBr, cm$^{-1}$): 3317, 2987, 2881, 1385, 1206 and 1060; $^1$H NMR: δ1.12 (3H, dd, J=6.0 Hz, J=2.4 Hz), 1.28 (3H, s), 1.41 (1H, d, J=10.8 Hz), 1.42 (3H, s), 1.66 (1H, d, J=10.8 Hz), 2.13 (1H, m), 2.24 (1H, s), 3.26 (1H, m), 3.32 (1H, s), 3.97 (1H, br s) and 4.12 (1H, d, J=5.6Hz); $^{13}$C NMR: δ20.1, 24.2, 25.5, 28.0, 42.2, 57.0, 61.3, 68.8, 80.7, 82.5 and 109.7; MS (El) m/z (relative intensity): 214 (M$^+$, 5), 198 (16), 138 (16), 110 (15), 82 (21) and 68 (100).

C) Preparation of Catalysts

EXAMPLE C1

Using Compound (108)

20 μmol of compound (108) and 1.53 mg (2.5 μmol) of [RuCl$_2$(p-cumene)]$_2$ are added to a flask and water present is then removed azeotropically using benzene. The benzene is then replaced by 2 ml of isopropanol and the mixture is stirred for 10 minutes. The solution is used directly in the transfer hydrogenation (catalyst K1).

EXAMPLE C2

Using Compound (109)

The procedure is as in example C1 and compound (109) is used (catalyst K2).

EXAMPLE C3

Using Compound (110)

The procedure is as in example C1 and compound (110) is used (catalyst K3).

EXAMPLE C4

Using Compound (111)

The procedure is as in example C1 and compound (111) is used (catalyst K4).

EXAMPLE C5

Using Compound (108)

The procedure is as in example C1 and compound (108) and (cyclopentadienylIrCl)$_2$ is used (catalyst K5).

EXAMPLE C6

Using Compound (108)

The procedure is as in example C1 and compound (108) and (cyclopentadienylRhCl)$_2$ is used (catalyst K6).

EXAMPLE C7

Using Compound (111)

The procedure is as in example C1 and compound (111) and (cyclopentadienylIrCl)$_2$ is used (catalyst K7).

EXAMPLE C8

Using Compound (111)

The procedure is as in example C1 and compound (111) and (cyclopentadienylRhCl)$_2$ is used (catalyst K8).

Comparative Example

The procedure is as in example C1 and 2 azanorbornyl-3-methanol is used (catalyst K9).

D) Use Examples

EXAMPLES D1–16

5 mmol of ketone (substrate) are dissolved in 48 ml of isopropanol and 20 μl (40 mmol) of 1 M potassium isopropoxide solution in isopropanol are added at room temperature, and then the catalyst solution. The mixture is then allowed to react at room temperature. The reaction is monitored by means of $^1$H NMR. The optical excess is determined by gas chromatography (capillary gas chromatograph with CP-Chirasil-Dex CB column using nitrogen as carrier gas).

The results are listed in table 1. S/C is the molar ratio of substrate to catalyst. Catalyst K4 is used in examples D1—D16.

TABLE 1

| Example | Ketone | S/C | Time (min) | Conversion % | ee (%) |
|---|---|---|---|---|---|
| D1 | Acetophenone | 200 | 6 | 96 | 96 |
| D2 | Acetophenone | 1000 | 15 | 95 | 96 |
| D3 | Isobutyrophenone | 200 | 30 | 93 | 90 |
| D4 | α,α,α-Trimethylacetophenone | 200 | 30 | 83 | 85 |
| D5 | 3-Methylacetophenone | 200 | 4 | 100 | 96 |
| D6 | 3-Methylacetophenone | 1000 | 15 | 90 | 96 |
| D7 | 3-Methoxyacetophenone | 200 | 4 | 100 | 98 |
| D8 | 3-Aminoacetophenone | 200 | 4 | 98 | 98.5 |
| D9 | 3-Nitroacetophenone | 200 | 4 | 100 | 91 |
| D10 | 3-Nitroacetophenone | 1000 | 15 | 100 | 90 |
| D11 | 4-Bromoacetophenone | 200 | 3 | 98 | 91 |
| D12 | 4-Chloroacetophenone | 1000 | 15 | 90 | 92 |
| D13 | 1-Acetonaphthone | 200 | 4 | 100 | 99.5 |
| D14 | 1-Acetonaphthone | 1000 | 15 | 98 | 99.5 |
| D15 | 3-Acetylpyridine | 200 | 4 | 98 | 89 |
| D16 | 4-Acetylpyridine | 200 | 3 | 97 | 91 |

EXAMPLE D17–D20

Comparative Example

The procedure is as in example D1 and acetophenone is used as substrate. The ratio S/C is 1 000. The results are indicated in table 2.

TOR is turnover rate [(mole of product/mole of catalyst)/h], which is calculated after 50% conversion.

TABLE 2

| Example | Catalyst | Conversion (%) | Time (h) | TOR | ee (%) |
|---|---|---|---|---|---|
| D17 | K1 | 92 | 1.0 | 3000 | 96 |
| D18 | K2 | 72 | 1.0 | 1900 | 95 |
| D19 | K3 | 90 | 1.0 | 2800 | 96 |
| D20 | K4 | 98 | 1.0 | 8500 | 96 |
| Comparative example | K9 | 90 | 3.0 | 1050 | 94 |

EXAMPLES D21–D29

The procedure is as in example D1 and the transfer hydrogenation is carried out using acetophenone. The results are indicated in table 3.

TABLE 3

| Example | Catalyst | S/C | Conversion (%) | Time (h) | ee (%) |
|---|---|---|---|---|---|
| D21 | K1 | 200 | 97 | 0.25 | 96 |
| D22 | K1 | 1000 | 90 | 1.0 | 96 |
| D23 | K5 | 200 | 98 | 20.0 | 89 |
| D24 | K6 | 200 | 94 | 2.0 | 96 |
| D25 | K4 | 200 | 98 | 0.1 | 96 |
| D26 | K4 | 1000 | 95 | 0.25 | 96 |
| D27 | K7 | 200 | 96 | 0.7 | 93 |
| D28 | K8 | 200 | 97 | 0.08 | 96 |
| D29 | K8 | 1000 | 77 | 1.0 | 96 |

What is claimed is:

1. A compound of the formula I, in the form of its racemates, mixtures of stereoisomers or mainly pure stereoisomers

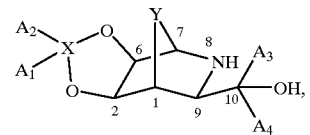
(I)

in which

Y is $C_1$–$C_4$alkylene or —$SiR_1R_2$—;

X is a carbon atom and $A_1$ and $A_2$ independently of one another are hydrogen, $C_1$–$C_{12}$alkyl, $C_2$–$C_{12}$alkenyl, $C_3$–$C_8$cycloalkyl, $C_3$–$C_8$cycloalkenyl, $C_3$–$C_8$cycloalkyl-$C_1$–$C_4$alkyl, $C_3$–$C_8$cycloalkenyl-$C_1$–$C_4$alkyl, $C_6$–$C_{10}$aryl or $C_7$–$C_{14}$aralkyl; or X is a silicon atom and $A_1$ and $A_2$ independently of one another are $C_1$–$C_{12}$alkyl, $C_3$–$C_8$cycloalkyl, $C_3$–$C_8$cycloalkyl-$C_1$–$C_4$alkyl, $C_6$–$C_{10}$aryl or $C_7$–$C_{14}$aralkyl;

$A_3$ and $A_4$ independently of one another are hydrogen, $C_1$–$C_{12}$alkyl, $C_3$–$C_8$cycloalkyl, $C_3$–$C_8$-cycloalkyl-$C_1$–$C_4$alkyl, $C_6$–$C_{10}$aryl or $C_7$–$C_{14}$aralkyl; and $R_1$ and $R_2$ independently of one another are $C_1$–$C_6$alkyl, cyclohexyl, phenyl or benzyl.

2. A compound according to claim 1, wherein Y is methylene or ethylene.

3. A compound according to claim 1, wherein X is a carbon atom.

4. A compound according to claim 1, wherein $A_3$ and $A_4$ are hydrogen, methyl or ethyl.

5. A compound according to claim 1, which has the formula Ia

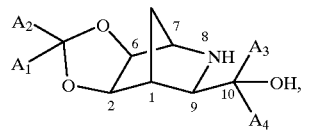
(Ia)

in which $A_1$ and $A_2$ independently of one another are hydrogen, $C_1$–$C_4$alkyl, $C_5$–$C_6$cycloalkyl, $C_5$–$C_6$-cycloalkylmethyl, phenyl or benzyl; and $A_3$ and $A_4$ independently of one another are hydrogen or $C_1$–$C_4$alkyl.

6. A compound according to claim 5, wherein $A_1$ and $A_2$ are each $C_1$–$C_4$alkyl, cyclohexyl or phenyl.

7. A process for the preparation of compounds of the formula I according to claim 1, in which (a) a compound of the formula II

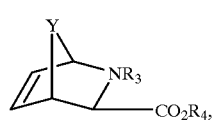
(II)

in which $R_3$ is hydrogen or a protective group, and $R_4$ is $C_1$–$C_4$alkyl, phenyl or benzyl, is reacted in an inert solvent with $OsO_4$ and subsequent hydrolysis to the cis-diol of the formula III (III)

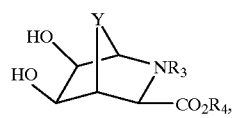

(b) the compound of the formula III is acetalized or ketalized to give a compound of the formula IV (IV)

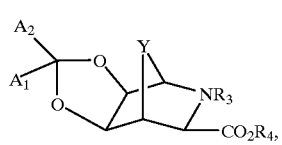

and
(c) if desired, after removal of the protective group, the compound of the formula IV is reduced to a compound of the formula I in which $A_3$ and $A_4$ are each hydrogen,
  (d1) or the ester group of the compound of the formula III is first reduced to the alcohol and then oxidized to the aldehyde of the formula V (V)

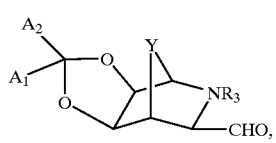

(d2) the compound of the formula V is reacted with a Grignard reagent comprising the group $A_4$ and, if desired, removal of the protective group $R_3$ to give a compound of the formula I in which $A_3$ is hydrogen and $A_4$ is a substituent as defined beforehand.

8. A compound of the formula VI (VI)

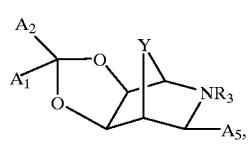

in which
  $A_1$, $A_2$ and Y are as defined in claim 1, $R_3$ hydrogen or a protective group, $A_5$ is the group —CH=O or —$CO_2$—$R_4$, and $R_4$ is $C_1$-$C_4$alkyl, phenyl or benzyl, excluding the compound where $A_1$ is methyl, $A_2$ is methyl, Y is methylene, $R_3$ is 1-phenyl-1-ethyl and $A_5$ is —$CO_2$-$R_4$ where $R_4$ is ethyl.

9. A metal complex of a metal selected from sub-group VIII of the Periodic Table of the Elements with a compound of the formula I according to claim 1 as a ligand.

10. A metal complex according to claim 9, wherein the metal is selected from the group consisting of Fe, Ni, Co, Rh, Pd, Ir, Ru and Pt.

11. A metal complex according to claim 9, wherein the metal is selected from the group consisting of Rh, Ir and Ru.

12. A metal complex which has the formula VII

[Ru(arene)(L)(A)]     (VII), in which A is hydride or chloride, and L is a ligand of the formula I according to claim 1.

13. A metal complex which has the formula VIII

[Me(diene)(L)(A6)]     (VIII), in which Me is Rh or Ir, diene is an open-chain or cyclic diene, L is a ligand of the formula I according to claim 1, and $A_6$ is halide.

14. A metal complex which has the formula IX

[Me1 Cp(L)A7]     (IX), in which $Me_1$ is Rh, Ir or Ru, A7 is hydride or halide, L is a ligand of the formula I according to claim 1, and Cp is a substituted or unsubstituted cyclopentadienyl or indenyl.

15. A process for asymmetric hydrogenation using hydrogen, or for transfer hydrogenation using hydrogen donors, of prochiral compounds having carbon/carbon or carbon/heteroatom multiple bonds, wherein the compounds are reacted at low to elevated temperatures in the presence of catalytic amounts of a metal complex according to claim 9.

16. A process according to claim 15, wherein the prochiral unsaturated compounds are alkenes, cycloalkenes, heterocycloalkenes, and open-chain or cyclic ketones, ketimines or ketohydrazones.

17. A process according to claim 15, wherein the ratio of substrate to catalyst is from 10 to 10 000.

18. A kit, comprising, in separate vessels, as component (a) a metal complex, a metal complex salt or a metal compound from the group consisting of the TM8 metals which are able to form a catalyst with a ligand, and as component (b) a compound according to claim 1 as the ligand.

19. A compound according to claim 8, wherein the protective group is benzyl, 1-phenyl-1-ethyl, diphenylmethyl or trityl.

20. A metal complex according to claim 13, wherein the halide is chloride, bromide or iodide.

21. A metal complex according to claim 14, wherein the halide is chloride.

* * * * *